US00PP14564P29

(12) United States Plant Patent
Kaagman

(10) Patent No.: US PP14,564 P2
(45) Date of Patent: Feb. 24, 2004

(54) DAHLIA PLANT NAMED 'DADA DEEP ROSE'

(50) Latin Name: *Dahlia variabilis*
Varietal Denomination: Dada Deep Rose

(75) Inventor: Pim Kaagman, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/404,821

(22) Filed: Apr. 1, 2003

(51) Int. Cl.[7] ..... A01H 5/00
(52) U.S. Cl. ..... Plt./321
(58) Field of Search ..... Plt./321

*Primary Examiner*—Bruce R. Campell
*Assistant Examiner*—A. Para
(74) *Attorney, Agent, or Firm*—Jondle & Associates PC

(57) ABSTRACT

A dahlia cultivar particularly distinguished by rose colored flowers, compact habit and good basal branching.

1 Drawing Sheet

Genus and species: *Dahlia variabilis.*
Variety denomination: 'Dada Deep Rose'.

BACKGROUND OF THE NEW PLANT

The present invention comprises a new and distinct cultivar of dahlia, botanically known as *Dahlia variabilis*, and hereinafter referred to by the cultivar name 'Dada Deep Rose'. The new cultivar is asexually reproduced from vegetative cuttings and tissue culture resulting from the cross of the seed/pod parent Dahlstar Burgundy (U.S. Plant Pat. No. 12,715)×DB-17-2, a deep rose proprietary line that is unnamed and unpatented.

'Dada Deep Rose' is a product of a planned breeding program intended to create new dahlia plants with rose colored flowers, compact habit, good basal branching and moderately vigorous growth.

The new cultivar was created in 1997 in Andijk, The Netherlands and has been asexually reproduced repeatedly by vegetative cuttings and tissue culture in Gilroy, Calif., Andijk, The Netherlands, and Guatemala over a four-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature inflorescence.

DESCRIPTION OF THE NEW CULTIVAR

The following detailed descriptions set forth the distinctive characteristics of 'Dada Deep Rose'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light. Plants had been cut back numerous times prior to data readings taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

Classification:
- *Botanical.*—*Dahlia variabilis.*
- *Commercial.*—Dahlia.

Growth:
- *Form.*—Upright, compact and mounding.
- *Growth and branching habit.*—Good vigorous habit, well branched, full plant.
- *Height.*—From soil level to top of blooms: Approximately 25–30 cm.
- *Width.*—Approximately 30–45 cm including flowers.
- *Time to produce a finished flowering plant.*—9–12 weeks.
- *Outdoor plant performance.*—Fast cropping, free flowering, used in patio planters and mixed container plantings or garden beds.
- *Time to initiate roots.*—Approximately 14–28 days in the greenhouse.
- *Root description.*—Fibrous, white.

Leaves:
- *Arrangement.*—Young foliage leaves are single and mature leaves simple, opposite.
- *Length.*—3.2–4.3 cm.
- *Width.*—2.8–2.9 cm.
- *Leaf blade shape.*—Ovate.
- *Leaf margin.*—Dentate/Ciliate.
- *Apex aspect.*—Apiculate.
- *Base aspect.*—Attenuate.
- *Leaf color.*—Upper surface, closest to RHS 139A (green) and Undersurface, RHS 191A (greyed-green) base color, with RHS# 137B (green) veining.
- *Texture.*—Hispid with strigulose on veins.
- *Venation.*—Pinnate.
- *Venation color.*—RHS 144B (yellow-green).
- *Petiole length.*—1.7–1.9 cm.
- *Petiole width.*—0.15–2.0 cm.
- *Petiole color.*—RHS 144B (yellow-green).
- *Petiole texture.*—Hispid.

Stem:

*Length.*—30–40 cm.

*Diameter.*—0.4–0.5 cm.

*Internodes length.*—0.3–0.5 cm.

*Color.*—Between RHS 144A and B (yellow-green).

*Texture.*—Smooth, occasional hispid.

*Stem anthocyanin.*—No.

*Peduncle color.*—RHS 144B (yellow-green).

*Peduncle length.*—2.5–3.5 cm.

*Peduncle diameter.*—0.2 cm.

*Peduncle texture.*—Smooth.

Bud:

*Shape.*—Orbicular.

*Diameter.*—0.7–1.0 cm.

*Length.*—0.6–0.8 cm.

*Color at tight bud.*—Close to RHS 59A (red-purple) when bracts divide.

Flower:

*Blooming habit.*—Continuous all through the growing season. Good floriferousness.

*Inflorescence type.*—Borne on terminals above foliage, semi-double flowers, floret faces upward or outward.

*Flower diameter.*— 3.5–4.5 cm.

*Ray petal color.*—Front side, RHS# 59A (red-purple) but lighter and Underside, RHS 61A (red-purple) base color with streaks of RHS 76C (purple) the length of the petal. Petal length — 1.6–1.7 cm. Petal width — 0.7–0.9 cm. Petal apex shape — Mucronulate. Petal base shape — Spathulate. Petal margin — Entire. Petal texture — Papillose. Petal quantity — 38–45.

*Disc petal color.*—RHS 14A (yellow-orange). Petal length — 0.6 cm. Petal diameter — 0.1 cm. Petal shape — Elongated, cylindrical, shiny. Petal quantity — 45–55.

*Involucral bracts.*—Usually 5, sometimes up to 7 or 8.

*Color.*—RHS 191A (greyed-green) base color with RHS 138A (green) veining.

*Length.*—0.8–0.9 cm.

*Width.*—0.4–0.5 cm.

*Shape.*—Ovate.

*Apex.*—Acute to mucronulate.

*Texture.*—Hispid.

*Lastingness of individual blooms.*—7–12 days.

*Fragrance.*—No.

Reproductive organs:

*Androecium, pollen color.*—RHS# 14A (yellow-orange).

*Gynoecium, stigma color.*—RHS# 12A (yellow).

*Style color.*—RHS 12B (yellow).

*Pistil length.*—0.7 cm.

*Fruit seed set.*—Not observed.

Disease and insect resistance: Not observed.

COMPARISON WITH KNOWN CULTIVARS

'Dada Deep Rose' differs from the female parent 'Dahlstar Burgundy' in the following ways: 'Dada Deep Rose' is a little more vigorous and has rose-colored flowers and 'Dahlstar Burgundy' is more burgundy color.

'Dada Deep Rose' differs from the male parent DB-17-2 in the following ways: 'Dada Deep Rose' is a small flower and is a compact plant and DB-17-2 is a regular size plant and flower.

I claim:

1. A new and distinct dahlia plant as shown and described herein.

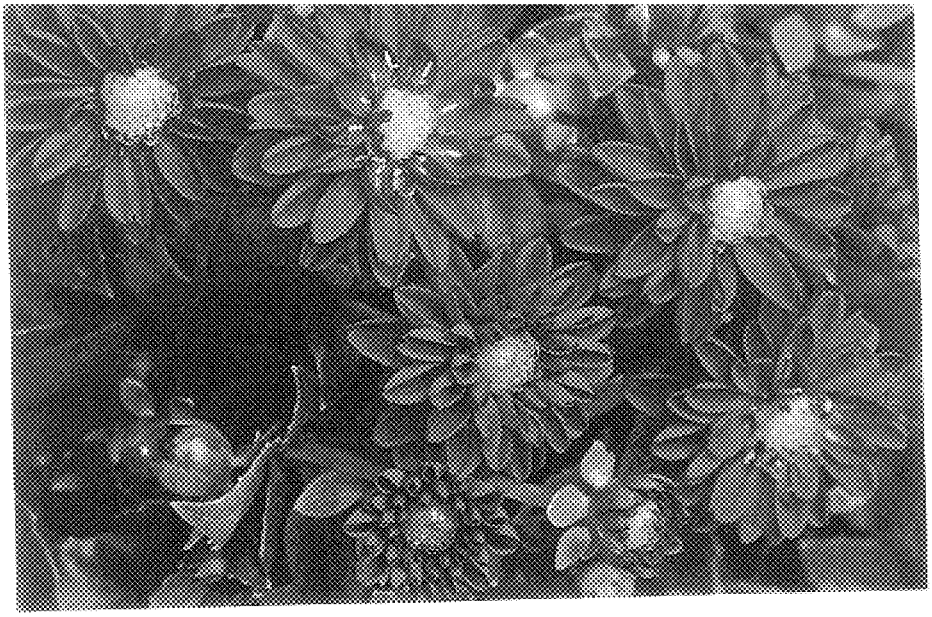

* * * * *